(12) United States Patent
Matsumoto et al.

(10) Patent No.: US 8,359,919 B2
(45) Date of Patent: Jan. 29, 2013

(54) THERMAL HUMIDITY SENSOR

(75) Inventors: Masahiro Matsumoto, Hitachi (JP);
Hiroshi Nakano, Hitachi (JP); Keiji Hanzawa, Mito (JP); Masamichi Yamada, Hitachinaka (JP)

(73) Assignee: Hitachi Automotive Systems, Ltd., Hitachinaka-shi (JP)

( * ) Notice: Subject to any disclaimer, the term of this patent is extended or adjusted under 35 U.S.C. 154(b) by 224 days.

(21) Appl. No.: 12/855,347

(22) Filed: Aug. 12, 2010

(65) Prior Publication Data

US 2011/0048127 A1 Mar. 3, 2011

(30) Foreign Application Priority Data

Aug. 28, 2009 (JP) ................. 2009-198159

(51) Int. Cl.
*G01N 27/12* (2006.01)
*G01N 27/18* (2006.01)
*G01F 1/69* (2006.01)

(52) U.S. Cl. ................. 73/335.05; 73/204.26
(58) Field of Classification Search ............ 73/335.05, 73/204.11, 202.5, 204.25, 204.26, 204.27, 73/25.02, 25.03, 25.04, 25.05
See application file for complete search history.

(56) References Cited

U.S. PATENT DOCUMENTS

| | | | |
|---|---|---|---|
| 5,837,884 A | 11/1998 | Kimura et al. | |
| 6,832,523 B2 * | 12/2004 | Benzel et al. | 73/763 |
| 2008/0016958 A1 | 1/2008 | Matsumoto et al. | |

FOREIGN PATENT DOCUMENTS

| | | |
|---|---|---|
| EP | 0 376 721 A2 | 7/1990 |
| EP | 0 376 721 A3 | 7/1990 |
| JP | 8-184576 A | 7/1996 |
| JP | 2008-2896 A | 1/2008 |
| JP | 2009-168649 A | 7/2009 |
| WO | WO 98/52027 A1 | 11/1998 |

OTHER PUBLICATIONS

R. Jachowicz, et al., "Sub-cooled water detection in silicon dew point hygrometer", Sensors and Actuators, Elsevier Sequoia, Aug. 25, 2000, pp. 75-83, vol. 85, No. 1-3, XP004214452.
European Search Report dated Nov. 30, 2010 (Three (3) pages).
Mitsuteru Kimura et al., "Proposal of Novel Absolute-Humidity Sensing Method Using a Pair of Diode-Thermistors and a Micro-Heater on a Micro-Air-Bridge", IEEE Sensors, EXCO, Oct. 22-25, 2006, pp. 948-951.
European Office Action dated Feb. 1, 2012 (Five (5) pages).

* cited by examiner

*Primary Examiner* — Lisa Caputo
*Assistant Examiner* — Punam Roy
(74) *Attorney, Agent, or Firm* — Crowell & Moring LLP

(57) ABSTRACT

Provided is a high-precision, mechanically robust thermal humidity sensor. A detecting element 1 of the thermal humidity sensor of the present invention has a diaphragm (a bridge structure) 2 formed on a planar substrate which is formed from a material with high thermal conductivity such as silicon or ceramic. Formed on the diaphragm 2 are temperature detecting resistors 4, 5, 6, and 7 and a heating resistor 3 arranged in a manner surrounding the temperature detecting resistors. Humidity is detected based on the outputs of the temperature detecting resistors 4, 5, 6, and 7. Accordingly, humidity measurement errors that can possibly occur due to the leakage of heat through the diaphragm 2 to the planar substrate can be reduced.

13 Claims, 8 Drawing Sheets

THERMAL HUMIDITY SENSOR

BACKGROUND OF THE INVENTION

1. Field of the Invention

The present invention relates to thermal humidity sensors, and for example, to thermal humidity sensors used in an environment in which vibrations frequently occur such as in vehicles.

2. Background Art

As an example of a humidity sensor, there is known a thermal humidity sensor that utilizes a phenomenon that the amount of heat radiated from a high-temperature element changes with the amount of water vapor in the air (for example, see Reference 1: JP Patent Publication (Kokai) No. 8-184576 A).

SUMMARY OF THE INVENTION

The thermal humidity sensor disclosed in Reference 1 that utilizes a phenomenon that the amount of heat radiated from a high-temperature element changes with the amount of water vapor in the air, however, has a problem in that heat radiated from the high-temperature element may escape by heat conduction through a supporting portion, whereby the probability of measurement errors could increase. In order to address such a problem, in the aforementioned conventional technique, a bridge structure is formed on a silicon substrate, and a supporting portion of the bridge structure is designed to be narrow, so that the heat escape due to the heat conduction is reduced.

However, designing the supporting portion of the bridge structure to be narrow could result in decreased mechanical strength thereof. In particular, if the sensor is used in an environment in which vibrations frequently occur such as in vehicles, the mechanical strength of the supporting portion of the bridge structure can be an important parameter.

The present invention has been made in view of the foregoing circumstances. It is an object of the present invention to provide a high-precision, mechanically robust thermal humidity sensor that can be used in an environment in which vibrations frequently occur such as in vehicles by preventing humidity measurement errors from occurring due to the leakage of heat through the supporting portion of the bridge structure, and thereby allowing the supporting portion of the bridge structure to be designed to be wide and strong.

A thermal humidity sensor in accordance with the present invention that solves the aforementioned problem has a temperature sensor, a heating element configured to generate heat in two heat generating positions that are opposite each other with the temperature sensor interposed therebetween, and humidity detecting means for detecting humidity based on the output of the temperature sensor.

According to the present invention, the temperature at a region between the two heat generating positions of the heating element is determined by the amount of heat radiated to the air, and humidity measurement errors that can possibly occur due to the leakage of heat through a supporting portion of a diaphragm portion (a bridge structure) can be reduced. Thus, the supporting portion of the diaphragm portion can be designed to be wide, and the mechanical strength thereof can thus be increased. Accordingly, a high-precision, vibration-resistant thermal humidity sensor can be provided that can be used in an environment in which vibrations frequently occur such as in vehicles.

DESCRIPTION OF SYMBOLS

Figure 1:
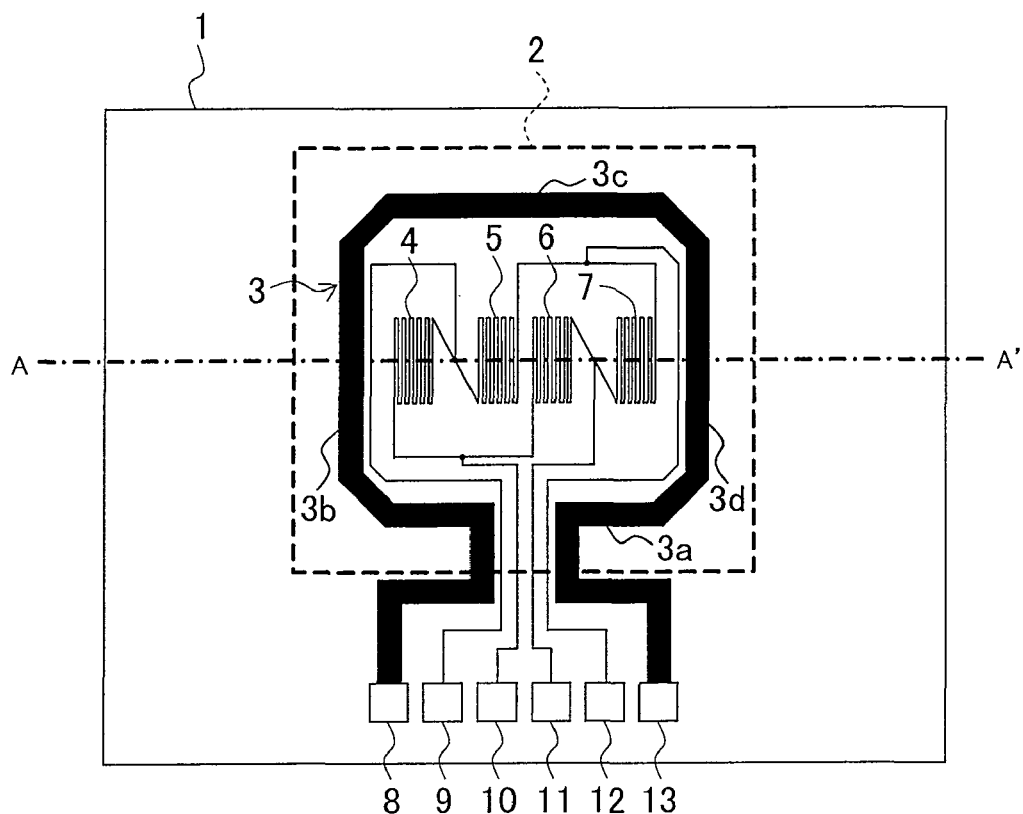
FIG. 1 is a plan view of a detecting element of a thermal humidity sensor in accordance with the first embodiment.

1 detecting element
2 diaphragm
3 heating resistor (heating element)
4-7 temperature detecting resistors
8-13 connecting terminals
14,15 insulating films
16 planar substrate
17 transistor
18 fixed resistor
19 differential amplifier
20,21 fixed resistors
22 differential amplifier
23 detecting element
24 diaphragm
25 ambient-temperature detecting resistor
26 heating resistor (heating element)
27 heating-element-temperature detecting resistor
28 temperature detecting resistor
29-36 connecting terminals
37 transistor
38 differential amplifier
39-41 fixed resistors
42 differential amplifier
43 detecting element
44,45 connecting terminals
46 diaphragm
47 heating resistor (heating element)
48-51 temperature detecting resistors
52 heating resistor (heating element)
53-58 connecting terminals
59 detecting element
60 connecting terminal
61 diaphragm
62 heating resistor (heating element)
63-65 thermocouple groups
66 heating resistor (heating element)
67-71 connecting terminals
72 detecting element
73-78 connecting terminals
79 diaphragm
80 temperature detecting resistor
81 heating resistor (heating element)
82-84 temperature detecting resistors

DETAILED DESCRIPTION OF THE PREFERRED EMBODIMENTS

Hereinafter, embodiments of the present invention will be described with reference to the accompanying drawings.

Figure 2:
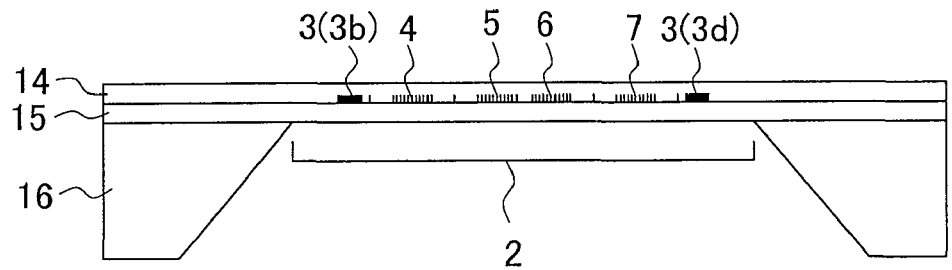
FIG. 2 is a cross-sectional view along line A-A' of FIG. 1.
Figure 3:
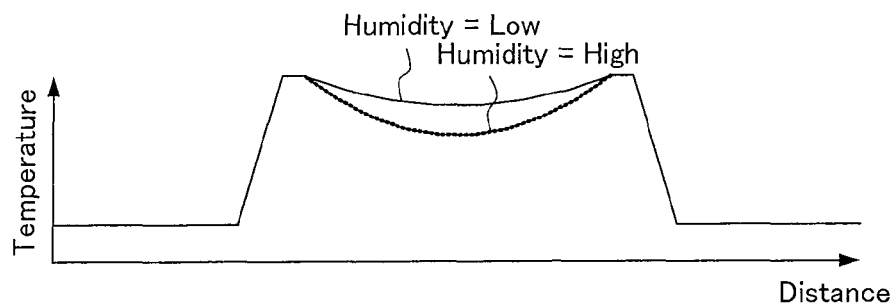
FIG. 3 is a temperature distribution diagram of the cross section along line A-A' of FIG. 1.
Figure 4:
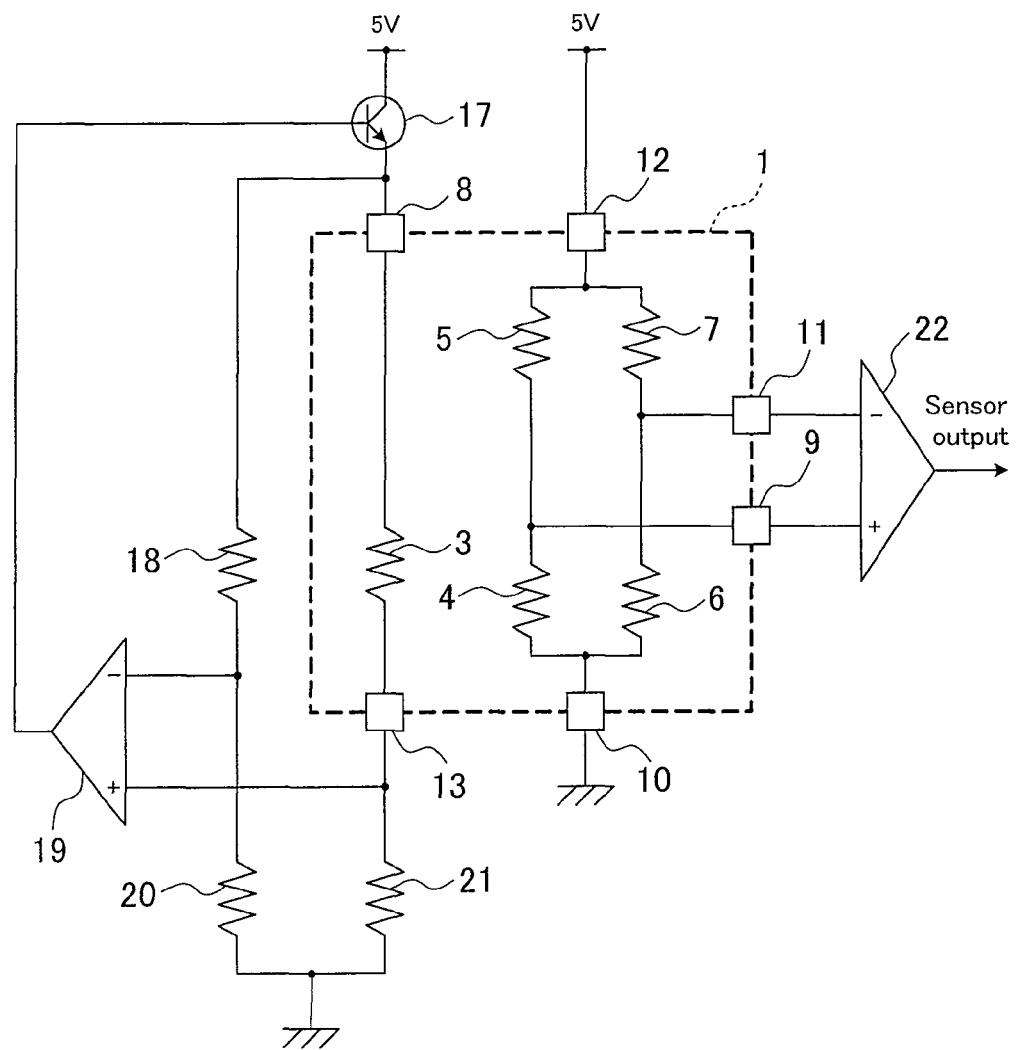
FIG. 4 is a diagram of a driving circuit of the thermal humidity sensor in accordance with the first embodiment.

First, a thermal humidity sensor in accordance with the first embodiment of the present invention will be described with reference to FIGS. 1, 2, 3, and 4. FIG. 1 is a plan view of a detecting element 1 of a thermal humidity sensor in accordance with the first embodiment. FIG. 2 is a cross-sectional view along line A-A' of FIG. 1. FIG. 3 is a temperature distribution diagram of the cross section along line A-A' of FIG. 1. FIG. 4 is a diagram of a driving circuit of the thermal humidity sensor in accordance with the first embodiment.

First, the configuration of the detecting element 1 of the present thermal humidity sensor will be described with reference to FIGS. 1 and 2. The detecting element 1 is formed by depositing insulating films 14 and 15 over a planar substrate 16, which is formed from a material with high thermal conductivity such as silicon or ceramic, and forming a diaphragm 2 on the planar substrate 16 by forming a space below the insulating films 14 and 15 by etching the planar substrate 16 from the back side thereof. The diaphragm 2 is a thin-film bridge structure formed of the insulating films 14 and 15. As the thermal conductivity of the insulating films 14 and 15 is low, the diaphragm 2 functions as a heat insulating portion.

Formed on the diaphragm 2 are a heating resistor 3, which is a loop-shaped heating element adapted to be heated to a predetermined temperature, and temperature detecting resistors 4, 5, 6, and 7 that are temperature sensors arranged on the inner side of the heating resistor 3. The heating resistor 3 has four linear portions 3a to 3d that are arranged in a continuous manner in a rectangular shape such that they surround the temperature detecting resistors 4, 5, 6, and 7. The position in which the linear portions 3a and 3b are arranged and the position in which the linear portions 3c and 3d are arranged correspond to two heat generating positions that are opposite each other with the temperature sensors interposed therebetween.

It should be noted that the heating resistor 3 is a resistor formed from a polysilicon thin film, a platinum thin film, a nickel alloy thin film, a molybdenum thin film, or the like. The heating resistor 3 generates heat with a current flow therethrough, and the temperature of the heating resistor 3 changes with the heat generated therefrom.

Each of the temperature detecting resistors 4, 5, 6, and 7 is also a resistor formed from a polysilicon thin film, platinum thin film, a nickel alloy thin film, a molybdenum thin film, or the like. A phenomenon that the resistance values of the temperature detecting resistors 4, 5, 6, and 7 change with temperature is utilized to detect the temperatures at places (intermediate position) where the temperature detecting resistors 4, 5, 6, and 7 are arranged.

The temperature detecting resistors 4, 5, 6, and 7 constitute a bridge circuit (temperature detecting means) configured to be capable of detecting the temperature difference between the temperature in the vicinity of the heating element 3 on the inner side of the heating resistor 3 and the temperature at the center of the region surrounded by the heating resistor 3. Herein, the temperature detecting resistors 4 and 7, which together function as one of the temperature sensors, are arranged closer to the linear portions 3b and 3d of the heating resistor 3 than the temperature detecting resistors 5 and 6, which together function as the other temperature sensor, are.

The heating resistor 3 is electrically connected to the outside via connecting terminals 8 and 13, and the bridge circuit composed of the temperature detecting resistors 4, 5, 6, and 7 is electrically connected to the outside via connecting terminals 9, 10, 11, and 12.

Next, the basic operation of the humidity sensor of this embodiment will be described. In the present humidity sensor, the heating resistor 3 is heated to a predetermined temperature. The higher the heating temperature is, the higher the sensitivity of the humidity sensor to humidity is. However, a temperature of 300 to 500° C. would be appropriate as the heating resistor 3 could otherwise deteriorate.

When the heating resistor 3 is heated to a predetermined temperature, the temperature distribution of the cross section along line A-A' of FIG. 1 becomes that shown in FIG. 3. That is, the temperature at a place where the heating resistor 3 is arranged (the heat generating position) is kept constant, whereas the temperature at the region surrounded by the heating resistor 3 decreases due to the radiation of heat to the air.

The amount of heat radiated to the air changes with the amount of humidity in the air. Thus, detecting a change in the temperature distribution with the temperature detecting resistors 4, 5, 6, and 7 allows a signal corresponding to the humidity to be extracted. It should be noted that measurement of the temperature distribution is carried out by detecting the temperature difference among the four positions in which the temperature detecting resistors 4, 5, 6, and 7 are arranged with the use of the bridge circuit composed of the temperature detecting resistors 4, 5, 6, and 7.

Herein, the temperature detecting resistors 4 and 7 are arranged in the vicinity of the heating resistor 3, and the temperature detecting resistors 5 and 6 are arranged at around the center of the region surrounded by the heating resistor 3, so that the output voltage of the bridge circuit composed of the temperature detecting resistors 4, 5, 6, and 7 will change with the change in the temperature distribution of the portion surrounded by the heating resistor 3.

In this embodiment, the temperature at the position in which the heating resistor 3 is arranged is kept constant. Thus, the temperature distribution of the region on the inner side of the heating resistor 3 is determined only by the heat radiated to the air. That is, the temperature distribution of the region on the inner side of the heating resistor 3 is not influenced by the radiation of heat from the heating resistor 3 to the planar substrate 16. Thus, there is no need to design the supporting portion of the diaphragm 2 to be narrow in order to reduce the amount of heat radiated from the heating resistor 3 to the planar substrate 16, and thus the strength of the supporting portion of the diaphragm 2 can be increased. Accordingly, even when this sensor is used in an environment in which vibrations frequently occur such as in vehicles, the supporting portion of the diaphragm 2 can be prevented from being damaged. Thus, a highly reliable humidity sensor can be provided.

In addition, in this embodiment, since an output corresponding to the humidity is obtained from the output voltage of the bridge circuit composed of the temperature detecting resistors 4, 5, 6, and 7, it is possible to easily obtain the ratiometric characteristics (characteristics that the output voltage varies in proportion to the power supply voltage) that are frequently used in applications of vehicles.

Further, when an output corresponding to the humidity is obtained from the bridge circuit composed of the temperature detecting resistors 4, 5, 6, and 7, it is also possible to suppress fluctuations in the sensor characteristics with respect to fluctuations in the resistance value of the heating resistor as compared to the conventional techniques. This is because, when the conventional method of determining the amount of heat generated by a heating resistor is used, a change in the resistance value of the heating resistor would directly influence the output of the sensor. However, when a signal corresponding to the humidity is obtained from the output voltage of a bridge circuit as in this embodiment, influence on the sensor characteristics can be suppressed to the minimum provided that the resistance values of all resistors that constitute the bridge change in a uniform manner.

Next, a driving circuit of the present thermal humidity sensor will be described with reference to FIG. 4. This driving circuit includes a transistor 17 that drives the heating resistor 3; fixed resistors 18, 20, and 21 that constitute the bridge circuit with the heating resistor 3; a differential amplifier 19 that amplifies the output voltage of the bridge circuit composed of the heating resistor 3 and the fixed resistors 18, 20, and 21 so as to drive the transistor 17; and a differential amplifier 22 that amplifies the output voltage of the bridge circuit composed of the temperature detecting resistors 4, 5, 6, and 7.

The output voltage of the bridge circuit composed of the heating resistor 3 and the fixed resistors 18, 20, and 21 of the present thermal humidity sensor changes with the temperature of the heating resistor 3 as the resistance value of the heating resistor 3 changes with the change in the temperature of the heating resistor 3. Thus, the temperature of the heating resistor 3 is detected from the output voltage of the bridge circuit composed of the heating resistor 3 and the fixed resistors 18, 20, and 21, and the amount of current fed to the heating resistor 3 is controlled by controlling the transistor 17 such that the temperature of the heating resistor 3 can be constant (temperature control means).

It should be noted that if the fixed resistors 18, 20, and 21 are provided with appropriate temperature coefficients, or if fixed resistors are connected in parallel or series with the heating resistor 3 so that the temperature of the heating resistor 3 will change with the change in the ambient temperature, it becomes also possible to change the sensitivity of the present thermal humidity sensor and thus to improve the temperature characteristics thereof.

Figure 5:
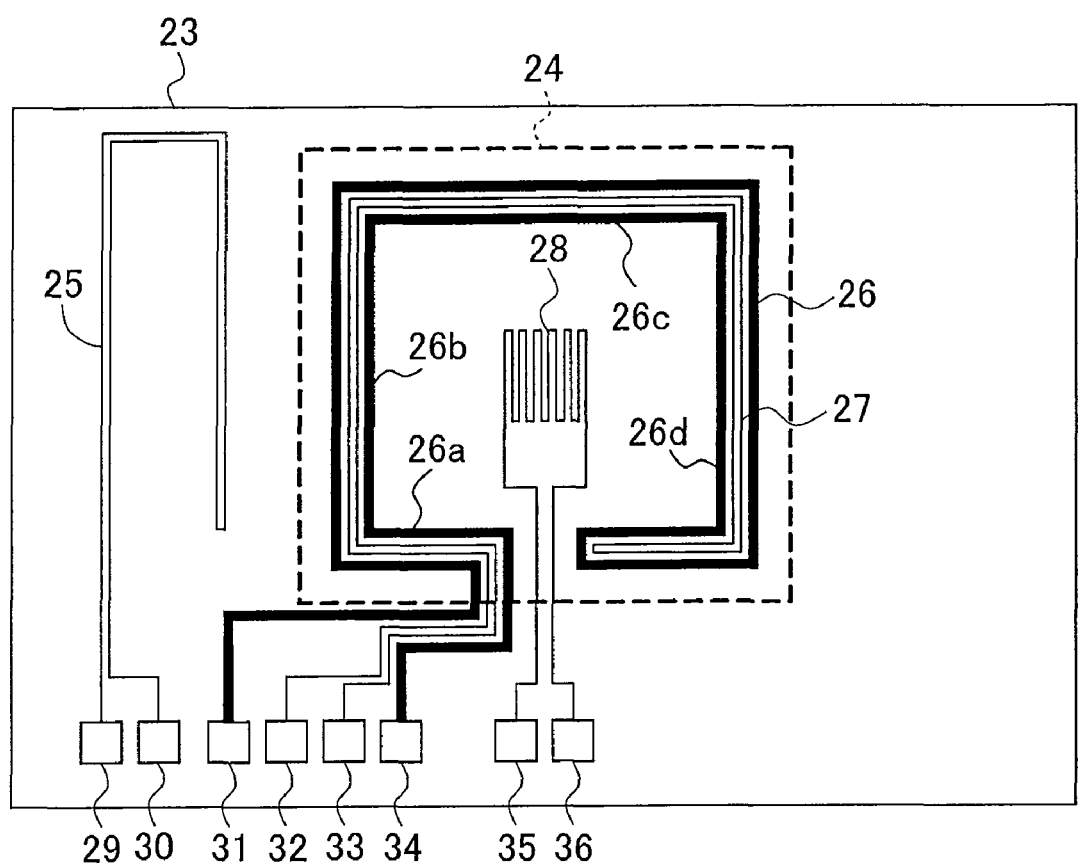
FIG. 5 is a plan view of a detecting element of a thermal humidity sensor in accordance with the second embodiment.
Figure 6:
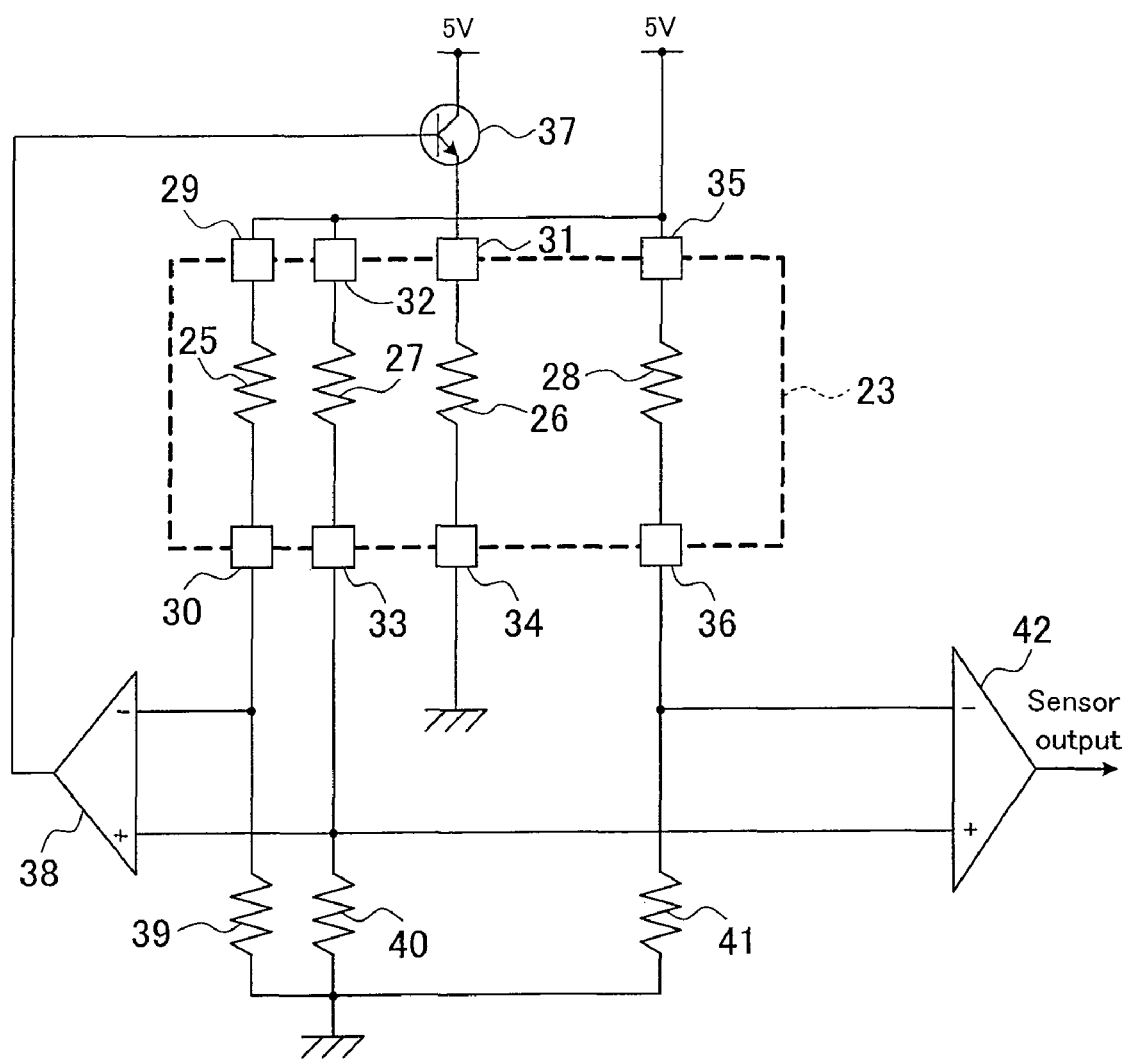
FIG. 6 is a diagram of a driving circuit of the thermal humidity sensor in accordance with the second embodiment.

Next, a thermal humidity sensor in accordance with the second embodiment of the present invention will be described with reference to FIGS. 5 and 6. FIG. 5 is a plan view of a detecting element of a thermal humidity sensor in accordance with the second embodiment, and FIG. 6 is a diagram of a driving circuit of the thermal humidity sensor in accordance with the second embodiment.

First, the configuration of a detecting element 23 of the present thermal humidity sensor will be described with reference to FIG. 5. It should be noted that the cross-sectional structure of the detecting element 23 has, as with the detecting element 1 described in the first embodiment, insulating films deposited over a planar substrate, which is formed from a material with high thermal conductivity such as silicon or ceramic, and a diaphragm 24 formed on the planar substrate by forming a space below the insulating films by etching the planar substrate from the back side thereof.

Formed on the diaphragm 24 are a heating resistor 26 that is a loop-shaped heating element adapted to be heated to a predetermined temperature; a heating-element-temperature detecting resistor 27 whose resistance value changes with the temperature of the heating resistor 26, the heating-element-temperature detecting resistor 27 being arranged in the vicinity of the heating resistor 26; a temperature detecting resistor (a temperature sensor) 28 arranged in a region surrounded by the heating resistor 26; and an ambient-temperature detecting resistor (an ambient temperature sensor) 25 whose resistance value changes with the ambient temperature, the ambient-temperature detecting resistor 25 being arranged on the outer side of the diaphragm 24 on the planar substrate.

The heating resistor 26 has four linear portions 26a to 26d that are arranged in a continuous manner in a rectangular shape such that they surround the temperature detecting resistor 28. The position in which the linear portions 26a and 26c are arranged and the position in which the linear portions 26b and 26d are arranged correspond to two heat generating positions that are opposite each other with the temperature sensor interposed therebetween.

The heating resistor 26 is a resistor formed from a polysilicon thin film, platinum thin film, a nickel alloy thin film, a molybdenum thin film, or the like. The heating resistor 26 generates heat with a current flow therethrough. Each of the heating-element-temperature detecting resistor 27, the temperature detecting resistor 28, and the ambient-temperature detecting resistor 25 is also a resistor formed from a polysilicon thin film, platinum thin film, a nickel alloy thin film, a molybdenum thin film, or the like. The resistance values of such resistors change with temperature.

The heating resistor 26 is electrically connected to the outside via connecting terminals 31 and 34. The heating-element-temperature detecting resistor 27 is electrically connected to the outside via connecting terminals 32 and 33. The temperature detecting resistor 28 is electrically connected to the outside via the connecting terminals 35 and 36. The ambient-temperature detecting resistor 25 is electrically connected to the outside via connecting terminals 29 and 30.

Next, a driving circuit of the present thermal humidity sensor will be described with reference to FIG. 6. This driving circuit includes a transistor 37 that drives the heating resistor 26; a bridge circuit composed of the heating-element-temperature detecting resistor 27, the ambient-temperature detecting resistor 25, and fixed resistors 39 and 40; a differential amplifier 38 that amplifies the output voltage of the bridge circuit composed of the heating-element-temperature detecting resistor 27, the ambient-temperature detecting resistor 25, and the fixed resistors 39 and 40 so as to drive the transistor 37; and a differential amplifier 42 that amplifies the output voltage of the bridge circuit composed of the heating-element-temperature detecting resistor 27, the temperature detecting resistor 28, and the fixed resistors 40 and 41.

In the driving circuit of the present thermal humidity sensor, the temperature difference between the temperature of the heating resistor 26 and the ambient temperature is detected from the output voltage of the bridge circuit composed of the heating-element-temperature detecting resistor 27, the ambient-temperature detecting resistor 25, and the fixed resistors 39 and 40. The amount of current fed to the heating resistor 26 is controlled by controlling the transistor 37 such that the temperature difference between the temperature of the heating resistor 26 and the ambient temperature can be constant (temperature control means).

It should be noted that if the fixed resistors 39 and 40 are provided with appropriate temperature coefficients, or if fixed resistors are connected in parallel or series with the heating-element-temperature detecting resistor 27 so that the heating temperature of the heating resistor 26 will change with the change in the ambient temperature, it becomes also possible to change the sensitivity of the present thermal humidity sensor and thus to improve the temperature characteristics thereof.

Even if the fixed resistors 39 and 40 are arranged on the planar substrate as with the ambient-temperature detecting resistor 25, this driving circuit will operate normally. In addition, as the amount of heat radiated from the heat generating portion to the air is proportional to the temperature of the air and the temperature of the heat generating portion, excellent temperature characteristics can be obtained by controlling the temperature difference between the ambient temperature and the heating resistor 26 to be constant as in the present driving circuit.

In addition, in the driving circuit of the present thermal humidity sensor, a signal corresponding to the humidity is obtained by detecting the difference between the temperature of the heating resistor 26 and that of the temperature detecting resistor 28 from the output voltage of the bridge circuit composed of the heating-element-temperature detecting resistor 27, the temperature detecting resistor 28, and the fixed resistors 40 and 41.

This is because, as the temperature distribution of the region surrounded by the heating resistor 26 of the humidity sensor in this embodiment changes with humidity as with the humidity sensor in accordance with the first embodiment, it is possible to detect changes in the temperature distribution by detecting the temperature of the temperature detecting resistor 28 and the temperature of the heating-element-temperature detecting resistor 27 with the use of the bridge circuit composed of the heating-element-temperature detecting resistor 27, the temperature detecting resistor 28, and the fixed resistors 40 and 41.

In the humidity sensor of this embodiment, the temperature at a place (intermediate position) where the heating resistor 26 is arranged is also kept constant. Thus, the temperature distribution of the region on the inner side of the heating resistor 26 (the temperature distribution of the region surrounded by the heating resistor 26) is determined only by the heat radiated to the air. That is, the temperature distribution of the region on the inner side of the heating resistor 26 is not influenced by the radiation of heat from the heating resistor 26 to the planar substrate.

Thus, there is no need to design the supporting portion of the diaphragm 24 to be narrow in order to reduce the amount of heat radiated from the heating resistor 26 to the planar substrate, and thus the strength of the supporting portion of the diaphragm 24 can be increased. Accordingly, even when this sensor is used in an environment in which vibrations frequently occur such as in vehicles, the supporting portion of the diaphragm 24 can be prevented from being damaged. Thus, a highly reliable humidity sensor can be provided.

Figure 7:
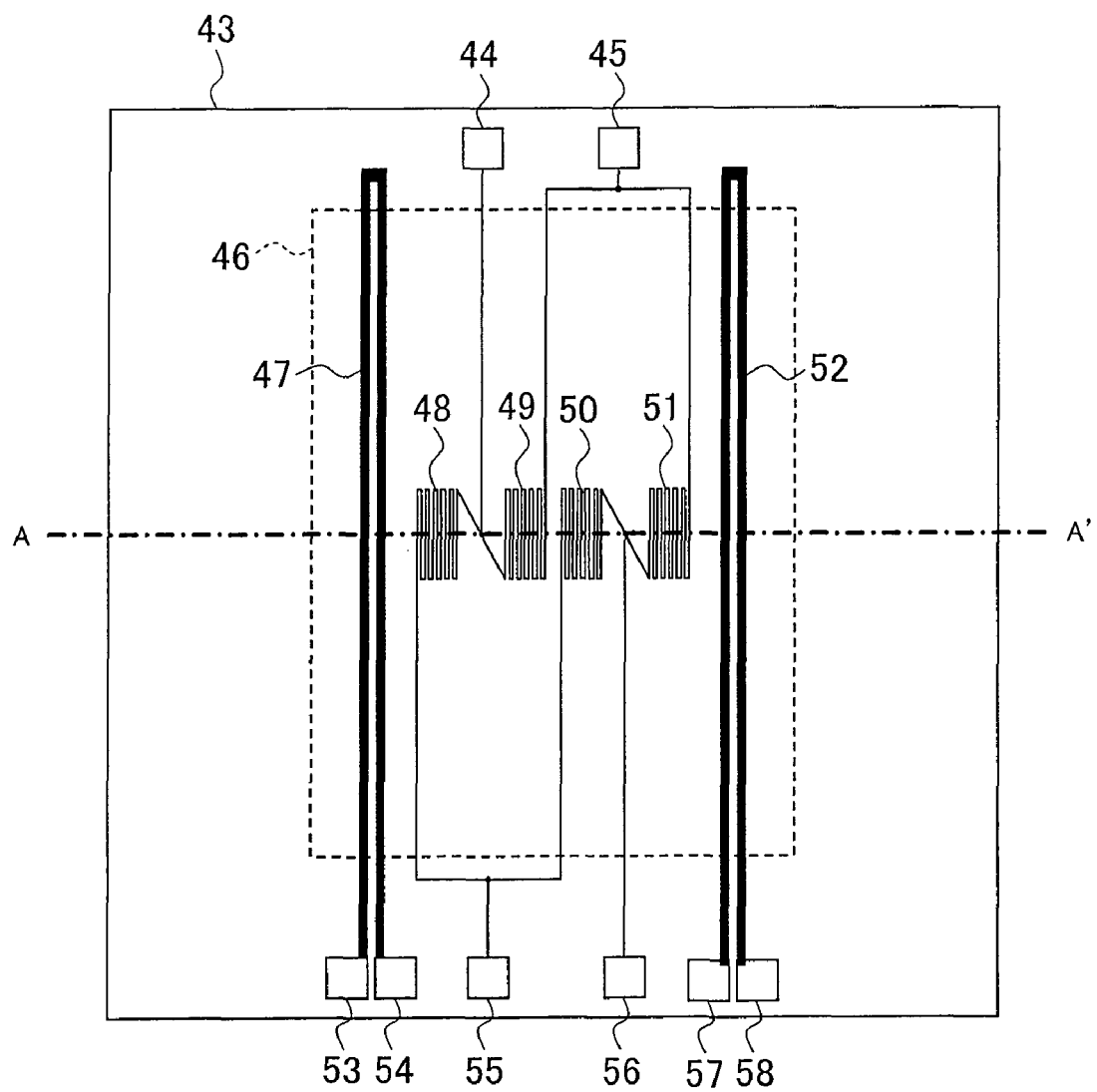
FIG. 7 is a plan view of a detecting element of a thermal humidity sensor in accordance with the third embodiment.

Next, a thermal humidity sensor in accordance with the third embodiment of the present invention will be described with reference to FIG. 7. FIG. 7 is a plan view of a detecting element of the thermal humidity sensor in accordance with the third embodiment.

First, the configuration of a detecting element 43 of the present thermal humidity sensor will be described with reference to FIG. 7. It should be noted that the cross-sectional structure of the detecting element 43 has, as with the detecting element 1 described in the first embodiment, insulating films deposited over a planar substrate, which is formed from a material with high thermal conductivity such as silicon or ceramic, and a diaphragm 46 formed on the planar substrate by forming a space below the insulating films by etching the planar substrate from the back side thereof.

Formed on the diaphragm 46 are heating resistors 47 and 52 adapted to be heated to a predetermined temperature, and temperature detecting resistors 48, 49, 50, and 51 arranged on the inner side of the heating resistors 47 and 52. The temperature detecting resistors 48, 49, 50, and 51 constitute a bridge circuit. The heating resistors 47 and 52 are paired with each other with the temperature detecting resistors 48, 49, 50, and 51 interposed therebetween, and run in parallel with each other. Specifically, the heating resistors 47 and 52 are arranged such that the length of the heating resistors 47 and 52 in the direction in which they run in parallel with each other is longer than the distance therebetween.

Each of the heating resistors 47 and 52 is a resistor formed from a polysilicon thin film, platinum thin film, a nickel alloy thin film, a molybdenum thin film, or the like. The heating resistors 47 and 52 generate heat with a current flow therethrough. Each of the temperature detecting resistors 48, 49, 50, and 51 is also a resistor formed from a polysilicon thin film, platinum thin film, a nickel alloy thin film, a molybdenum thin film, or the like. The resistance values of such resistors change with temperature.

The heating resistor 47 is electrically connected to the outside via connecting terminals 53 and 54. The heating resistor 52 is electrically connected to the outside via connecting terminals 57 and 58. The bridge circuit composed of the temperature detecting resistors 48, 49, 50, and 51 is also connected to the outside via connecting terminals 55, 56, 44, and 45.

Next, the basic operation of the present thermal humidity sensor will be described. In the present humidity sensor, the heating resistors 47 and 52 are heated to a predetermined temperature. When the heating resistors 47 and 52 are heated to a predetermined temperature, the temperature distribution of a cross section along line A-A' of FIG. 7 becomes that shown in FIG. 3 described in the first embodiment. That is, the temperatures at places where the heating resistors 47 and 52 are arranged (the heat generating positions) are kept constant, whereas the temperature at the region on the inner side of the heating resistors 47 and 52 decreases due to the radiation of heat to the air, whereby temperature distribution such as the one shown in FIG. 3 is generated.

The amount of heat radiated to the air changes with the amount of humidity in the air. Thus, detecting a change in the temperature distribution with the temperature detecting resistors 48, 49, 50, and 51 allows a signal corresponding to the humidity to be extracted.

In this embodiment, the heating elements 47 and 52 are arranged only in the two directions (right and left) shown in FIG. 7. Thus, the length of the diaphragm 46 in the perpendicular direction of FIG. 7 is designed to be longer than the distance between the heating elements 47 and 52, so that heat radiation in the perpendicular direction of FIG. 7 would not influence the temperature distribution. It should be noted that measurement of the temperature distribution is carried out by detecting the temperature difference among the four positions in which the temperature detecting resistors 48, 49, 50, and 51 are arranged with the use of the bridge circuit composed of the temperature detecting resistors 48, 49, 50, and 51.

Herein, the temperature detecting resistors 48 and 51 are arranged in the vicinity of the heating resistors 47 and 52, and the temperature detecting resistors 49 and 50 are arranged at around the center of the region interposed between the heating resistors 47 and 52, so that the output voltage of the bridge circuit composed of the temperature detecting resistors 48, 49, 50, and 51 will change with the change in the temperature distribution of the region interposed between the heating resistors 47 and 52.

In this embodiment, the temperatures at places (intermediate position) where the heating resistors 47 and 52 are arranged are also kept constant. Thus, the temperature distribution of the region on the inner side of the heating resistors 47 and 52 is determined only by the heat radiated to the air. That is, the temperature distribution of the region on the inner side of the heating resistors 47 and 52 is not influenced by the radiation of heat from the heating resistors 47 and 52 to the planar substrate.

That is, there is no need to design the supporting portion of the diaphragm 46 to be narrow in order to reduce the amount of heat radiated from the heating resistors 47 and 52 to the planar substrate, and thus the strength of the supporting portion of the diaphragm 46 can be increased.

Accordingly, even when this sensor is used in an environment in which vibrations frequently occur such as in vehicles, the supporting portion of the diaphragm 46 can be prevented from being damaged. Thus, a highly reliable humidity sensor can be provided. It should be noted that in this embodiment, the heating elements 47 and 52 are arranged only in the two directions (right and left) shown in FIG. 7. Thus, wires of the bridge circuit composed of the temperature detecting resistors 48, 49, 50, and 51 can be extracted to both the top and bottom sides in FIG. 7, whereby wiring on the diaphragm 46 can easily be accomplished.

Figure 8:
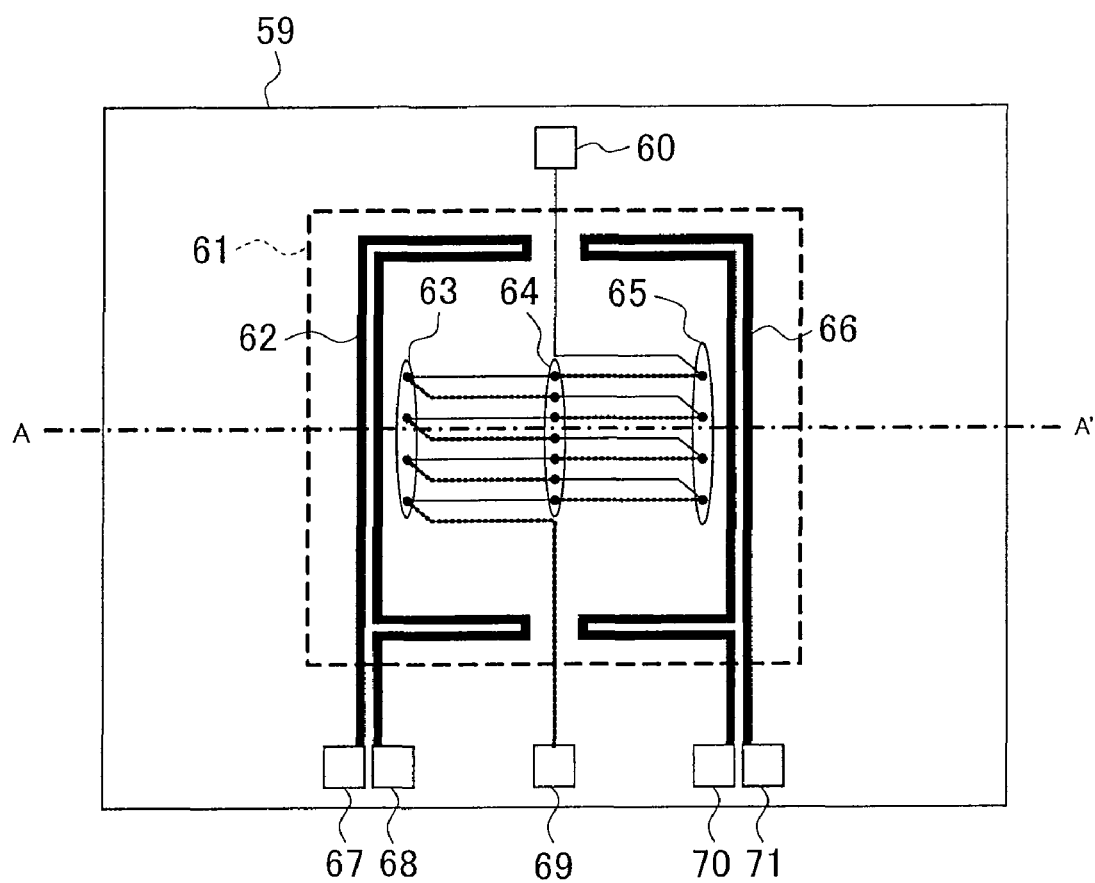
FIG. 8 is a plan view of a detecting element of a thermal humidity sensor in accordance with the fourth embodiment.

Next, a thermal humidity sensor in accordance with the fourth embodiment of the present invention will be described with reference to FIG. 8. FIG. 8 is a plan view of a detecting element of the thermal humidity sensor in accordance with the fourth embodiment.

First, the configuration of a detecting element 59 of the present thermal humidity sensor will be described with reference to FIG. 8. It should be noted that the cross-sectional structure of the detecting element 59 has, as with the detecting element 1 described in the first embodiment, insulating films deposited over a planar substrate, which is formed from a material with high thermal conductivity such as silicon or ceramic, and a diaphragm 61 formed on the planar substrate by forming a space below the insulating films by etching the planar substrate from the back side thereof.

Formed on the diaphragm 61 are heating resistors 62 and 66 adapted to be heated to a predetermined temperature, and thermocouple groups 63, 64, and 65 arranged on the inner side of the heating resistors 62 and 66. The heating resistors 62 and 66 are approximately U-shaped and are arranged opposite each other in a manner surrounding the thermocouple groups 63, 64, and 65.

Each of the heating resistors 62 and 66 is a resistor formed from a polysilicon thin film, platinum thin film, a nickel alloy thin film, a molybdenum thin film, or the like. The heating resistors 62 and 66 generate heat with a current flow therethrough. Each of the thermocouple groups 63, 64, and 65 is formed from polysilicon and metal (e.g., platinum, nickel alloy, or a molybdenum). The output voltages of the thermocouple groups 63, 64, and 65 change with the difference in temperature.

Each of the thermocouple groups 63, 64, and 65 is formed by connecting a plurality of thermocouples in series in order to increase the sensitivity. The heating resistor 62 is electrically connected to the outside via connecting terminals 67 and 68. The heating resistor 66 is electrically connected to the outside via connecting terminals 70 and 71. The thermocouple groups 63, 64, and 65 are electrically connected to the outside via connecting terminals 60 and 69.

Next, the basic operation of the present thermal humidity sensor will be described. In the present humidity sensor, the heating resistors 62 and 66 are heated to a predetermined temperature. When the heating resistors 62 and 66 are heated to a predetermined temperature, the temperature distribution of a cross section along line A-A' of FIG. 8 becomes that shown in FIG. 3 described in the first embodiment. That is, the temperatures at places where the heating resistors 62 and 66 are arranged (the heat generating positions) are kept constant, whereas the temperature at the region on the inner side of the heating resistors 62 and 66 decreases due to the radiation of heat to the air, whereby temperature distribution such as the one shown in FIG. 3 is generated.

The amount of heat radiated to the air changes with the amount of humidity in the air. Thus, detecting changes in the temperature distribution with the thermocouple groups 63, 64, and 65 allows a signal corresponding to the humidity to be extracted. In this embodiment, as the temperature distribution is detected with the thermocouple groups 63, 64, and 65, self-heating can be reduced than when temperature detecting resistors are used. Thus, highly accurate detection of humidity is possible.

Figure 9:
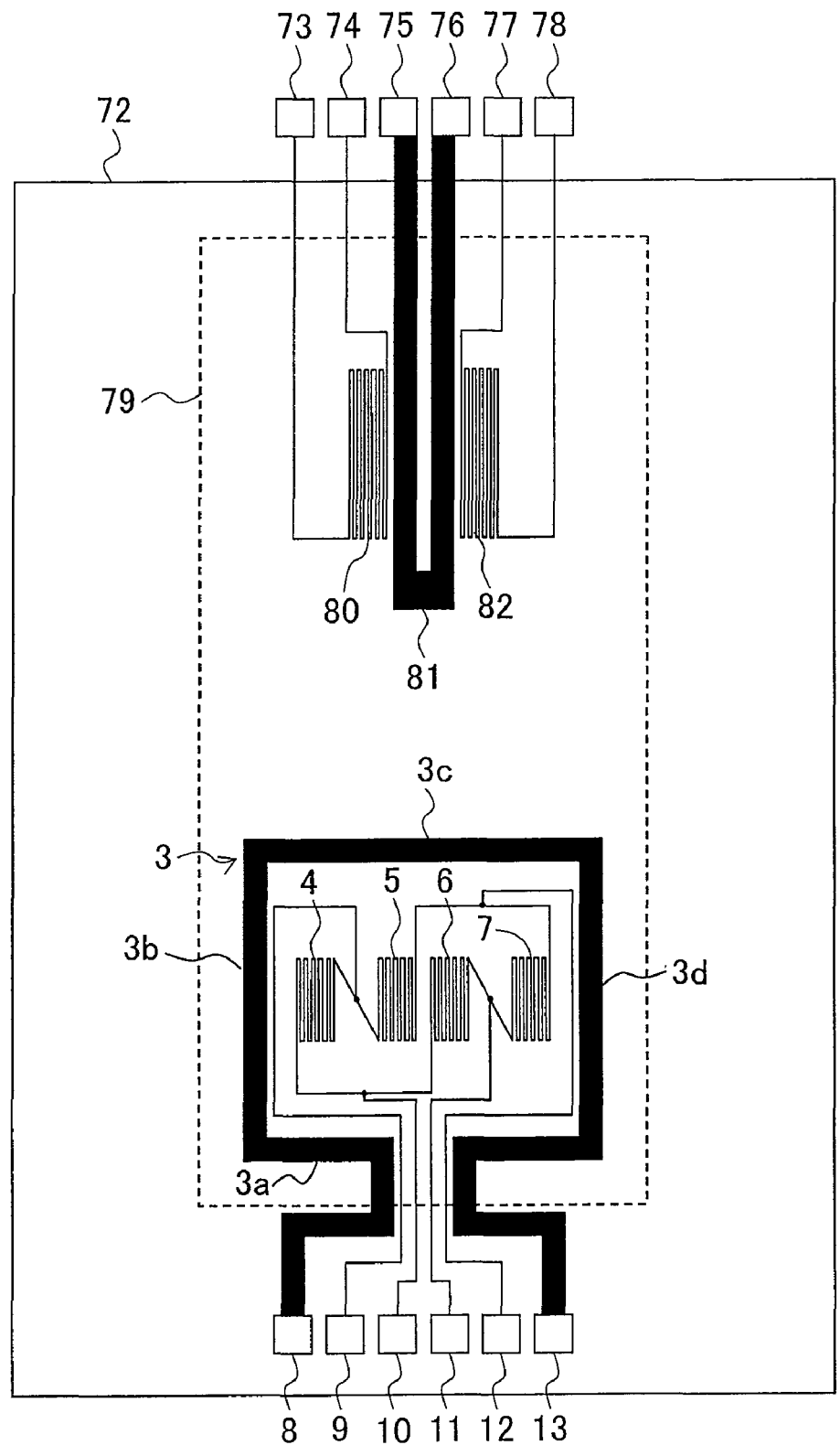
FIG. 9 is a plan view of a detecting element of a thermal humidity sensor in accordance with the fifth embodiment.

Next, a thermal humidity sensor in accordance with the fifth embodiment of the present invention will be described. FIG. 9 is a plan view of a detecting element of a thermal humidity sensor in accordance with the fifth embodiment.

First, the structure of a detecting element 72 of the present thermal humidity sensor will be described with reference to FIG. 9. A humidity detecting portion of the detecting element 72 arranged on the lower side of FIG. 9 is identical to that of the first embodiment. In this embodiment, a thermal air flow detecting portion is arranged on the upper side of FIG. 9. The thermal air flow detecting portion in this embodiment is arranged on the same diaphragm 79 as the humidity detection portion, whereby the chip size is reduced.

The air flow detecting portion of this embodiment includes a heating resistor 81, temperature detecting resistors 80 and 82 arranged on opposite sides of the heating resistor 81, and connecting terminals 73, 74, 75, 76, 77, and 78. The air flow detecting portion of this embodiment can be formed with the same cross-sectional structure as that of the humidity detecting portion. Thus, the air flow detecting portion can be arranged on the same diaphragm 79 without the need of changing the manufacturing process. It should be noted that as a conventional thermal air flow meter, there is known a technique disclosed in JP Patent Publication (Kokai) No. 2008-2896 A, for example.

Figure 10:
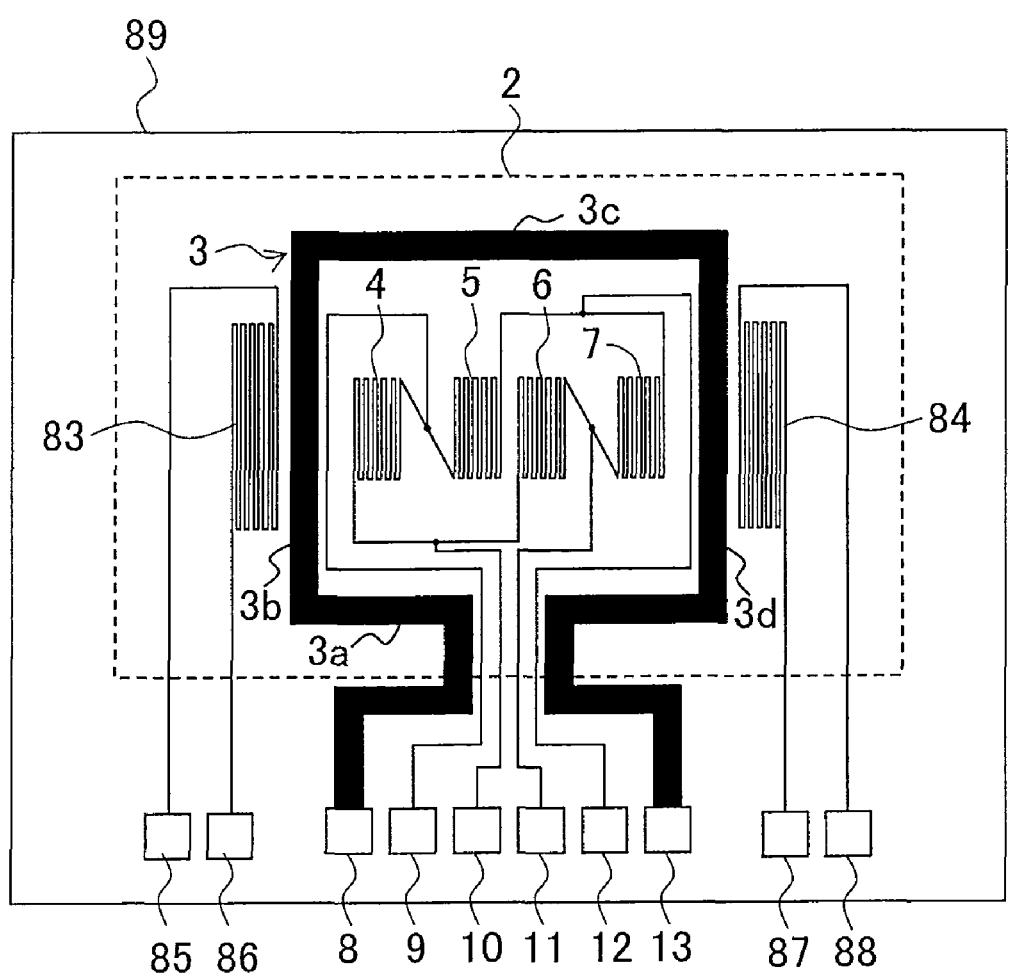
FIG. 10 is a plan view of a detecting element of a thermal humidity sensor in accordance with the sixth embodiment.

Next, a thermal humidity sensor in accordance with the sixth embodiment of the present invention will be described with reference to FIG. 10. FIG. 10 is a plan view of a detecting element of a thermal humidity sensor in accordance with the sixth embodiment.

First, the configuration of a detecting element 89 of the present thermal humidity sensor will be described with reference to FIG. 10. It should be noted that a humidity detecting portion of the detecting element 89 is identical to that of the first embodiment. In this embodiment, temperature detecting resistors 83 and 84 and connecting terminals 85, 86, 87, and 88 are added on opposite sides of the heating resistor 3, and the temperature difference between the opposite sides of the heating resistor 3 is detected, so that a signal corresponding to the air flow rate is obtained. It should be noted that as a conventional thermal air flow meter, there is known a technique disclosed in JP Patent Publication (Kokai) No. 2008-2896 A, for example.

The signal corresponding to the air flow rate obtained herein can also be used to compensate the output signal of the humidity sensor. In the thermal humidity sensor, an air flow above the detecting element 89 can be a cause of errors. This is because the amount of heat radiated from the heating element to the air could change due to the air flow. In order to eliminate such influence, the humidity sensor of this embodiment is provided with the temperature detecting resistors 83 and 84 on the opposite sides of the heating resistor 3 to measure the air flow rate, whereby the output signal of the sensor can be compensated based on such a signal. It should be noted that the signal obtained by measuring the air flow rate with the detecting element 89 can also be used as it is as an air flow signal.

What is claimed is:

1. A thermal humidity sensor comprising:
a plurality of temperature sensors;
a heating element configured to generate heat in two heat generating positions that are opposite each other with the plurality of temperature sensors interposed therebetween;
humidity detecting means for detecting humidity based on outputs of the plurality of temperature sensors; and
temperature detecting means for detecting a temperature at an intermediate position between the two heat generating positions based on the outputs of the plurality of temperature sensors,
wherein the humidity detecting means detects humidity based on the temperature detected by the temperature detecting means.

2. The thermal humidity sensor according to claim 1, wherein the heating element has a loop shape that surrounds the plurality of temperature sensors.

3. The thermal humidity sensor according to claim 1, wherein the heating element has a pair of heating elements that run in parallel with each other.

4. The thermal humidity sensor according to claim 3, wherein a length of the pair of heating elements in a direction in which the heating elements run in parallel with each other is longer than a distance between the pair of heating elements.

5. The thermal humidity sensor according to claim 1, wherein
the temperature detecting means detects a temperature distribution of a region between the two heat generating positions based on the outputs of the plurality of temperature sensors, and
the humidity detecting means detects humidity based on the temperature distribution detected by the temperature detecting means.

6. The thermal humidity sensor according to claim 1, wherein
the intermediate position includes a plurality of intermediate positions,
the temperature detecting means detects a temperature difference between at least two intermediate positions, and
the humidity detecting means detects humidity based on the temperature difference detected by the temperature detecting means.

7. The thermal humidity sensor according to claim 1, comprising at least two temperature sensors, wherein one of the temperature sensors is arranged closer to the heat generating position than the other temperature sensor is.

8. The thermal humidity sensor according to claim 1, further comprising temperature control means for controlling a temperature of the heating element constant.

9. The thermal humidity sensor according to claim 8, wherein the temperature control means changes the temperature of the heating element in accordance with an ambient temperature.

10. The thermal humidity sensor according to claim 8, wherein the temperature control means controls the temperature of the heating element so that a temperature difference between the temperature of the heating element and the ambient temperature is constant.

11. The thermal humidity sensor according to claim 1, wherein the heating element and the temperature sensor are arranged on a heat insulating portion provided on a silicon substrate.

12. The thermal humidity sensor according to claim 11, further comprising an ambient temperature sensor arranged on the silicon substrate, the ambient temperature sensor being configured to detect the ambient temperature.

13. The thermal humidity sensor according to claim 11, further comprising a thermal flow meter arranged on the silicon substrate.

* * * * *